US00PP15730P2

(12) United States Plant Patent
Olesen et al.

(10) Patent No.: US PP15,730 P2
(45) Date of Patent: Apr. 26, 2005

(54) ROSE PLANT NAMED 'POULEN005'

(50) Latin Name: *Rosa hybrida*
Varietal Denomination: POULen005

(75) Inventors: L. Pernille Olesen, Fredensborg (DK); Mogens N. Olesen, Fredensborg (DK)

(73) Assignee: Poulsen Roser A/S, Fredensborg (DK)

( * ) Notice: Subject to any disclaimer, the term of this patent is extended or adjusted under 35 U.S.C. 154(b) by 31 days.

(21) Appl. No.: 10/738,156

(22) Filed: Dec. 16, 2003

(51) Int. Cl.[7] ..... A01H 5/00
(52) U.S. Cl. ..... Plt./130
(58) Field of Search ..... Plt./130

*Primary Examiner*—Anne Marie Grunberg
*Assistant Examiner*—Annette H Para

(57) ABSTRACT

A new garden rose plant of the hybrid tea class which has abundant, lavender flowers and attractive foliage. This new and distinct variety has shown to be uniform and stable in the resulting generations from asexual propagation.

2 Drawing Sheets

Botanical classification: *Rosa hybrida.*
Variety denomination: 'POULen005'.

SUMMARY OF THE INVENTION

The present invention constitutes a new and distinct variety of garden rose plant which originated from a controlled crossing between the female seed parent plant, an unnamed seedling, and issued on Sep. 5, 1995 and the male parent, 'Evening star', a non-patented variety. The two parents were crossed during the summer of 1991 and the resulting seeds were planted in a controlled environment in Fredensborg, Denmark. The new variety is named 'POULen005'.

The new variety may be distinguished from its seed parent, by the following combination of characteristics:

1. The seed parent has a white or near white flower color. 'POULen005' has a mauve flower color.
2. The seed parent ha a medium growth height of 60 cm to 100 cm. 'POULen005' has a tall growth height of 100 cm to 150 cm.

The new variety may be distinguished from its pollen parent, by the following combination of characteristics:

1. The pollen parent has a white flower color. 'POULen005' has a mauve flower color.
2. The pollen parent has a slight fragrance. 'POULen005' has a strong floral fragrance.

The objective of the hybridization of this rose variety was to create a new and distinct variety for garden use with unique qualities, such as:

1. Uniform and abundant mauve flowers;
2. Vigorous, but compact growth when propagated both as a budded rose and on its own roots;
3. Disease resistance;
4. Exceptional fragrance.

This combination of qualities is not present in previously available commercial cultivars of this type, known to the inventors, and distinguish 'POULen005' from all other varieties of which we are aware.

As part of their rose development program, L. Pernille Olesen and Mogens N. Olesen germinated the seeds from the aforementioned hybridization during winter 1991 and conducted evaluations on the resulting seedlings in a controlled environment in Fredensborg, Denmark.

'POULen005' was selected in the spring 1992 by the inventors as a single plant from the progeny of the aformentioned hybridization.

Asexual reproduction of 'POULen005' by traditional budding and rooted cuttings was first done by L. Pernille and Mogens N. Olesen in their nursery in Fredensborg, Denmark in July, 1992. This initial and other subsequent asexual propagation conducted in controlled environments have demonstrated that the characteristics of 'POULen005' are true to type and are transmitted from one generation to the next.

BRIEF DESCRIPTION OF THE DRAWING

The accompanying color illustration shows as true as is reasonably possible to obtain in color photographs of this type, the typical characteristics of the buds, flowers, leaves, and stems, of 'POULen005'.

Specifically illustrated in Sheet 1:

FIG. 1.1; Open flower; stem showing open flower, the attachment of leaves and peduncles;

FIG. 1.2; Flower bud closed, flower bud as sepals unfold, and partially open;

Specifically illustrated in Sheet 2:

FIG. 2.1; Sepals, receptacle, and peduncle;
FIG. 2.2; Flower petals, detached;
FIG. 2.3; Leaves;
FIG. 2.4; Bare stem exhibiting thorns.

DETAILED DESCRIPTION OF THE VARIETY

The following is a description of 'POULen005', as observed in its growth in a field nursery in Jackson County, Oreg. Observed plants are 3 years of age, grown on *Rosa multiflora* understock. Color references are made under The Royal Horticultural Society (London, England) Colour Chart, 1995, except where common terms of color are used.

For a comparison several physical characteristics of the rose variety 'POULen005', a rose variety from the same inventors described and illustrated in U.S. Plant Pat. No. 13,293 and issued on Dec. 3, 2002 are compared to 'POULen005' in Chart 2.

CHART 1

| | 'POULen005' | 'POULscots' |
|---|---|---|
| General tonality | Violet Group 84C | Purple Group 76C. |
| Diameter of open flower | 80 to 100 mm. | 100 to 150 mm. |
| Petal size | 60 to 65 mm (l) × 55 to 60 mm (w). | 30 to 35 mm (l) × 36 mm (w). |

Parents:

*Seed parent.*—Unnamed seedling.

*Pollen parent.*—Evening Star.

FLOWER AND FLOWER BUD

Blooming habit: Recurrent.

Flower bud:

*Size.*—Upon opening, 45 mm in length from base of receptacle to end of bud.

*Bud form.*—Pointed ovoid.

*Bud color.*—As sepals unfold, petals are Greyed-White Group 156C to Violet Group 84D with intonations of Red-Purple Group 67A and Yellow-Green Group 145C. Sepals: Upper surface: Color: Yellow-Green Group 144B. Texture: Moderately pubescent. Lower surface: Color: Yellow-Green Group 144A. Texture: Moderately pubescent. Stipitate glands sparse. Weak to medium intensity of anthocyanic pigmentation the color of Greyed-Purple 184A. Shape: Sepal apex is cirrose. Base is flat at union with receptacle. Margins have medium foliaceous appendages on three of the five sepals. Size: 35 mm (l)×10 to 13 mm (w).

*Receptacle.*—Surface texture: Smooth and glabrous. Shape: Urn-shaped. Size: 11 mm (h)×12 mm (w). Color: Yellow-Green Group 144A.

*Peduncle.*—Surface: Smooth and glabrous with very few stipitate glands. Length: 60 to 65 mm. Color: Yellow-Green Group 144A. Strength: Strong.

*Borne.*—Singularly.

*Anthocyanin.*—None observed.

Flower bloom:

*Fragrance.*—Strong floral.

*Duration.*—The blooms have a duration on the plant of approximately 7 to 10 days. Afterwards, petals fall cleanly away from plant.

*Size.*—80 to 100 mm when open.

*Form.*—General shape is a deep cup. Shape of flower when viewed from the side: Upon opening, upper part: Flattened convex. Upon opening, lower part: Concave. Open flower, upper part: Flattened convex. Open flower, lower part: Concave.

*Petalage.*—30 petals under normal conditions with 10 petaloids.

Color:

*Upon opening, petals.*—Outermost petals: Outer side: Violet Group 84C to 84D. Inner side: Violet Group 84C to 84D. Innermost petals: Outer side: Violet Group 84C to 84D. Inner side: Violet Group 84C to 84D.

*Upon opening, basal petal spots.*—Outermost petals: Outer side: Yellow Group 2D. Inner side: Yellow Group 2D. Innermost petals: Outer side: Yellow Group 2D. Inner side: Yellow Group 2D.

*After opening, petals.*—Outermost petals: Outer side: Violet Group 84C to 84D. Inner side: Violet Group 84C to 84D. Innermost petals: Outer side: Violet Group 84C to 84D. Inner side: Violet Group 84C to 84D.

*After opening, basal petal spots.*—Outermost petals: Outer side: Yellow Group 2D. Inner side: Yellow Group 2D. Innermost petals: Outer side: Yellow Group 2D. Inner side: Yellow Group 2D.

General tonality: On open flower Violet Group 84C. No change in the general tonality at the end of the 10th day. Afterwards, general tonality is Violet Group 84C.

Petals:

*Petal reflex.*—Petals reflex very strongly. Margin: Entire and uniform with weak undulations of margin. Shape: Apex is round. Base is acute. Size: 60 to 65 mm (l)×55 to 60 mm (w). Texture: Smooth. Thickness: Average. Arrangement: Not formal.

*Petaloids.*—Quantity: 10 to 12 in number. Color: Violet Group 84C to 84D. Size: 38 to 40 mm (l)×35 to 38 mm (w).

Reproductive organs:

*Pistils.*—Length: 5 mm long. Quantity: 85.

*Pollen.*—Color: Greyed-Yellow Group 162A. Quantity: Scant.

*Anthers.*—Size: 2 to 4 mm long. Color: Greyed-Yellow Group 160C. Quantity: 101 (actual count).

*Filaments.*—Color: Greyed-Yellow Group 162D. Length: 10 to 12 mm.

*Stigmas.*—Interior in location to anthers. Color: Greyed-Yellow Group 162B.

*Styles.*—Color: Greyed-Yellow Group 162D.

*Hips.*—None observed in the field nursery in Jackson County, Oreg.

PLANT

Plant growth: Moderate, upright to bushy. When grown as a budded field grown plant on *Rosa multiflora* understock, the average height of the plant is 60 to 100 cm. The average width is 80 cm.

Stems:

*Color.*—Young wood: Yellow-Green Group 146C. Older wood: Yellow-Green Group 146B.

*Surface texture.*—Young wood: Smooth. Older wood: Smooth.

*Anthocyanin.*—Greyed-Purple Group 185A (weak).

*Thorns.*—Incidence: 4 thorns per 10 cm of stem. Size: Average length: 4 mm. Color: Greyed-Purple Group 185A. Shape: Deeply concave.

Plant foliage: Normal number of leaflets on normal leaves in middle of the stem: 7 leaflets.

*Compound leaf size.*—150 mm (l)×110 mm (w).

*Quantity.*—Average.

*Color.*—Mature foliage: Upper leaf surface: Yellow-Green Group 147A. Lower leaf surface: Yellow-Green Group 147C. Juvenile foliage: Upper leaf surface: Yellow-Green Group 146A. Lower leaf surface: Yellow-Green Group 147C.

Plant leaves and leaflets:

*Stipules.*—Size: 15 to 25 mm in length. Color: Yellow-Green Group 146B. Margins: Finely serrated. Anthocyanin: Location: At margins of juvenile foliage. Color: Greyed-Purple Group 185A.

*Petiole.*—Length: 20 to 35 mm. Color: Yellow-Green Group 144B. Underneath: Spines/prickles. Stipitate glands upper surface. Anthocyanin: Greyed-Red Group 181B.

*Rachis.*—Length: 20 to 35 mm. Color: Yellow-Green Group 144B. Underneath: Spines/prickles. Stipitate glands on upper surface. Anthocyanin: Color: Greyed-Red Group 181B.

*Leaflet.*—Size: 50 to 60 mm (l)×32 to 45 mm (w). Edge: Serrated. Shape: Generally ovate. Leaf apex is round. Base is acute. Texture: Smooth. Arrangement: Odd pinnate. Venation: Reticulate. Glossiness: Glossy to moderately glossy. Thickness: Thick.

Disease resistance: Above average resistance to mildew, rust, black spot, and Botrytis under normal growing conditions in Jackson County, Oreg.

Cold hardiness: The variety 'POULen005' has been found to be cold tolerant to USDA Cold Hardiness Zone 6.

We claim:

1. A new and distinct variety of rose plant of the hybrid tea rose class, substantially as herein illustrated and described as a distinct and novel rose variety due to its abundant lavender flowers, disease resistance, and extended period of bloom.

* * * * *

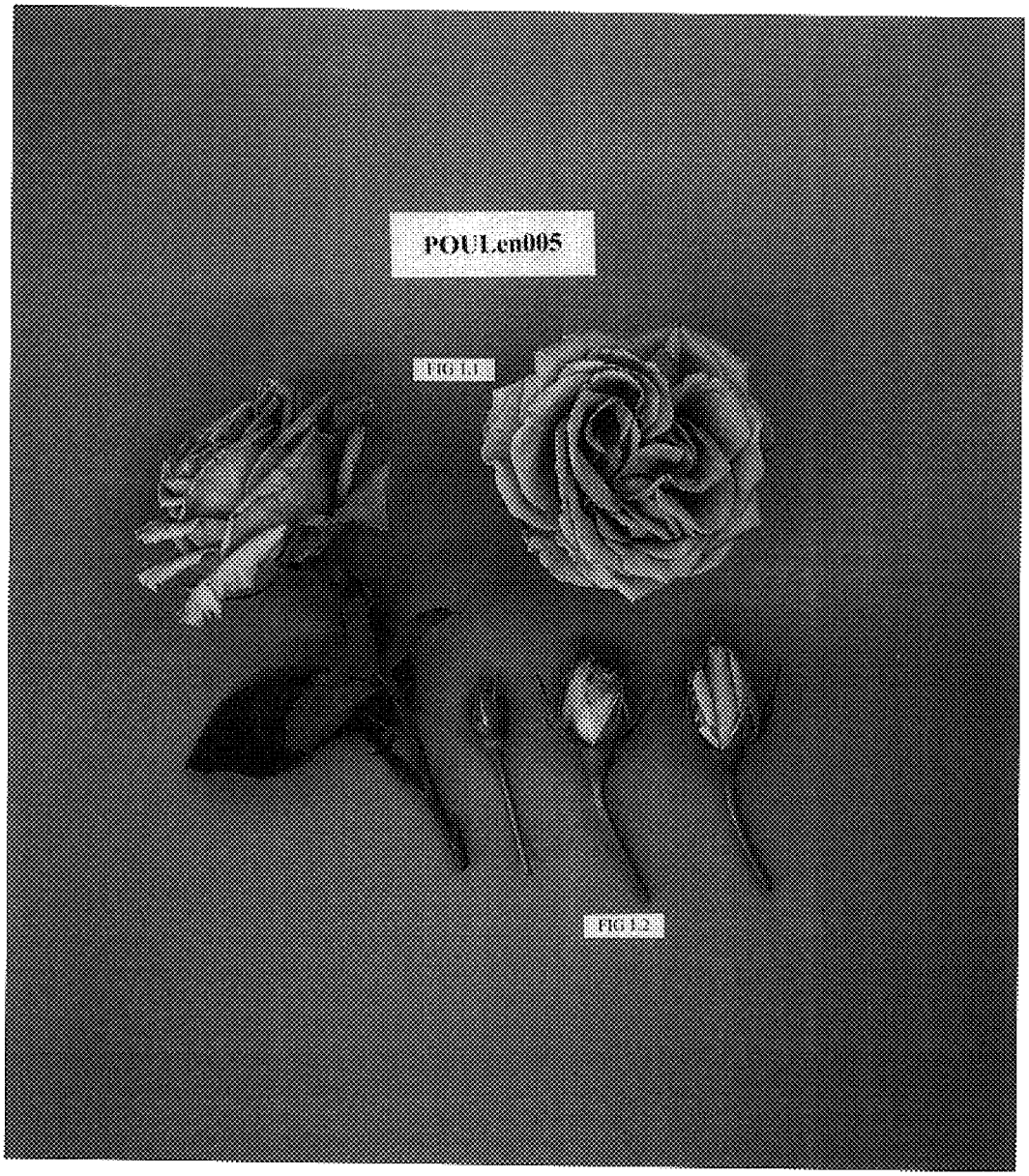
POULen005
FIG 1.1
FIG 1.2

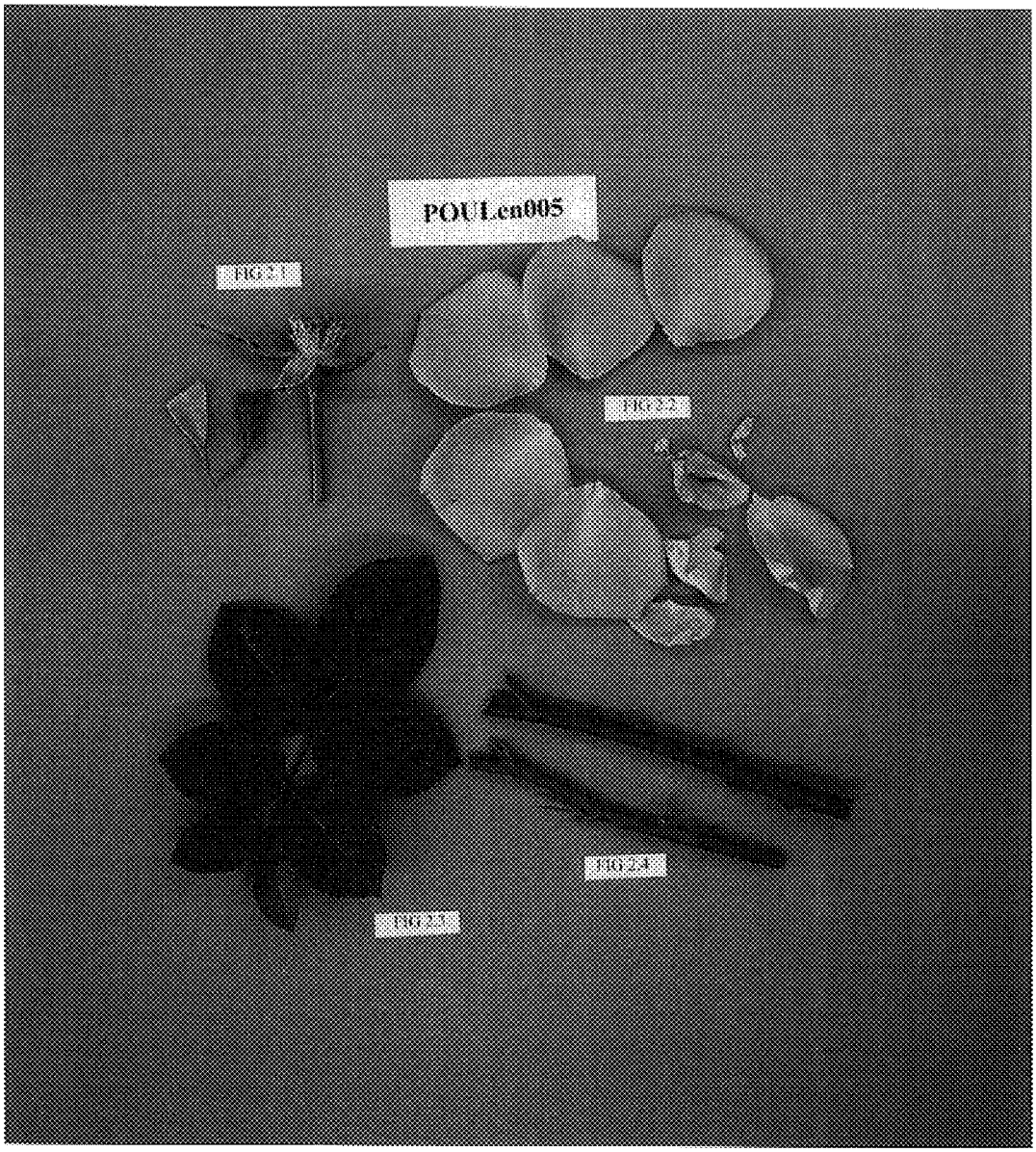
POULen005
FIG.2.1
FIG.2.2
FIG.2.3
FIG.2.4